(12) United States Patent
Myers et al.

(10) Patent No.: US 6,423,315 B1
(45) Date of Patent: *Jul. 23, 2002

(54) SYNTHETIC PEPTIDE FOR TREATMENT OF AUTOIMMUNE ARTHRITIS

(75) Inventors: Linda K. Myers; Jerome M. Seyer; Andrew H. Kang, all of Memphis, TN (US)

(73) Assignee: The University of Tennessee Research Corp., Knoxville, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/425,175

(22) Filed: Apr. 20, 1995

Related U.S. Application Data

(63) Continuation of application No. 08/025,570, filed on Mar. 3, 1993, now abandoned.

(51) Int. Cl.[7] .................. A61K 38/08; A61K 38/39; C07K 14/78; C07K 7/06
(52) U.S. Cl. .................. 424/185.1; 424/184.1; 424/192.1; 424/810; 424/198.1; 514/12; 514/17; 514/15; 514/13; 514/14; 514/16; 514/825; 530/300; 530/326; 530/327; 530/328; 530/329; 530/356; 530/806; 530/324; 530/325
(58) Field of Search .................. 424/185.1, 184.1, 424/192.1, 810, 198.1; 514/12, 17, 15, 13, 14, 16, 825; 530/300, 326, 327, 328, 329, 356, 806, 324, 325

(56) References Cited

U.S. PATENT DOCUMENTS 5,260,422 A * 11/1993 Clark et al.

OTHER PUBLICATIONS

Myers, Dialog, File FEDRIP, 00278068, Analog Peptides in Collagen–Induced Arthritis.,*
Seyer et al., Eur. J. Bio Chem, 181: 159–173, 1989.*
David, APMIS, 98: 575–584, 1990.*
Holmdahl et al., Imm. Rev., 118: 193–232, 1990.*
Myers et al., J. Immunol., 161: 3589–3595, 1998 (Abstract Thereof).*
McColl et al., Ann. Rheumat. Dis, 56: 240–246, 1997 (Abstract Thereof).*
Moder et al., Regional Immunology, 4: 305–313, 1992.*
Edgington, Bio/Technology, 10: 383–386, 388, 389, 1992.
Myers et al., Clin. Res., vol. 39; 852 A, 1991.
Ranges et al., *Prevention of Type II Collagen–Induced Arthritis By In Vivo Treatment With Anti–L3T4*, The Rockefeller University Press, 162:1105–1110.
Anderson et al., "Role of Mis–1 Locus and Clonal Deletion of T Cells in Susceptibility To Collagen–Induced Arthritis In Mice," 147: 1189–1193.
Adorini et al., *Peptide Competition for Antigen Presentation*, Immunology Today, vol. 11: 24, 1990.
Myers et al., "Identification of An Immunosuppressive Epitope of Type II Collagen That Confers Protection Against Collagen–Induced Arthritis", 170:1999–2010, 1989.
Wraith et al., "Antigen Recognition in Autoimmune Encephalomyelitis and the Potential for Peptide–Mediated Immunotherapy", *Cell*, 59:247–255, 1989.
Stuart et al., "Collagen–Induced Arthritis in Rats, Arthritis and Rheumatism", *Arthritis Rheumatism 22*, 1979.
Andriopoulos et al., "Antibodies to Native and Denatured Collagens in Sera of Patients with Rheumatoid Arthritis", *Arthritis Rheumatism*, 19, 1976.
Miller, "Isolation and Characterization of the Cyanogen Bromide Peptides from the $\alpha 1$ (II) Chain of Chick Cartilage Collagen", *Biochem.* 10, 1971.
Myers et al., "Characterization of a Tolerogenic T Cell Epitope of Type II Collagen and its Relevance to collagen–Induced Arthritis", *Immunol.*, 149:1439–1443, 1992.
Stuart et al., "Monkeying Around with Collagen Autoimmunity and Arthritis", *Lab. Invest.*, 54:1986.
Burraik et al., "Suppression of Collagen Type II–induced Arthritis By Transfer of Lymphoid Cells From Rats Immunized with Collagen", *Clin. Exp. Immunol.* 61:368–372, 1985.
Adorini et al., "Interaction of An Immunodominant Epitope With Ia Molecules In T–Cell Activation", *Proc. Natl. Acad. Sci*, USA 85:5181–5185, 1988.
Cremer et al., "Collagen–Induced Arthritis in Rats: Antigen–Specific Suppression of Arthritis and Immunity By Intravenously Injected Native Type II Collagen", *J. Immunol.*, 131, 1983.
Englert et al., "Suppression of Type II Collagen–Induced Arthritis by the Intravenous Administration of Type II Collagen or its Constituent Peptide $\alpha 1$ (II) $CB_{10}$", *Cell. Immunol.* 87:357–365, 1984.

(List continued on next page.)

*Primary Examiner*—Ronald B. Schwadron
(74) *Attorney, Agent, or Firm*—Howard Eisenberg, Esq.

(57) ABSTRACT

Peptides that are capable of suppressing autoimmune arthritis are disclosed. The polypeptides described by the present invention which are capable of suppressing autoimmune arthritis in mammals include analogues of CII 245-270. The peptides do not provoke a material immunogenic response from T cells, and thus are useful therapeutic agents for suppressing autoimmune arthritis, rheumatoid arthritis, juvenile arthritis, psoriatic arthritis, spondylo arthritis, relapsing polychondritis and other connective tissue diseases. A method of surpressing autoimmune arthritis in mammals is also provided by the present invention.

11 Claims, 3 Drawing Sheets

OTHER PUBLICATIONS

Guery et al., "Selective Immunosuppression by Administration of Major Jistocompatibility Complex (MHC) Class II–binding Peptides. I. Evidence For In Vivo MHC Blockade Preventing T Cell Activation", *J. Exp. Med.,* 175:1345–1352, 1992.

Kotake et al., "Analysis of the Pivotal Residues of the Immunodominant and Highly Uveitogenic Determinant of Interphotoreceptor Retinoid–Binding Protein", *Immunol.,* 146:2995–3001, 1991.

Kresina, "Down–Regulation of Murine Collagen–Induced Arthritis by a T Cell Hybridoma", *Expl. Cell Biol.* 56:860–102, 1988.

Kresina et al., "Adoptive Transfer of Suppression of Arthritis in the Mouse Model of Collagen–induced Arthritis", *J. Clin. Invest.,* 75:1990–1998, 1985.

Clayton et al., "Peptide–Specific Prevention of Experimental Allergic Encephalomyelitis", *J. Exp. Med.* 169::1681–1691, 1989.

DeMagistria et al., "Antigen Analog–Major Histocompatibility Complexes Act As Antagonists of the T Cell Receptor", *Cell,* 68:625–634, 1992.

Milich, "Functional Identification of Agretopic and Epitopic Residues Within an HBcAG T Cell Determinant", *Immunol.,* 143:3141–3147, 1989.

Oki et al., "T Cell Tolerance Studies At the Level of Antigenic Determinants", *J. Exp. Med.,* 161:897–911. 1985.

Buus et al., "The Interaction Between Protein–Derived Immunogenic Peptides and Ia", *Immunol. Rev,* 1987, No. 98.

Kappler et al., "Antigen Presentation by Ia$^+$ B cell Hybridomas to H–2 restricted T cell Hybridomas", *Proc. Natl. Acad. Sci.,* USA, 79:3604–3607, 1982.

Konomi et al., "Peptide specific Antibodies Identify the α2 Chain as the Proteoglycan Subunit of Type IX Collagen", *Biol. Chem.,* 261:6742–6746, 1986.

Wooley, et al., "Passive Transfer of Arthritis to Mice by Injection of Human Anti–Type II Collagen Antibody", *May Clin. Proc.,* 59:737–743, 1984.

Babbitt et al., "Antigen Competition at the Level of Peptide–1a Binding", *Proc. Natl. Acad. Sci.* USA 83:4509–4513, 1986.

Sakai et al., "Prevention of Experimental Encephalomyelitis With Peptides That Block Interaction of T Cells With Major Histocompatibility Complex Proteins", *Proc. Natl. Acad. Sci.* USA, 86 (1989).

Lamont et al., "Inhibition of Experimental Autoimmune Encephalomyelitis Induction of SIL/J Mice By Using a Peptide With High Affinity For IA$_s$ Molecules$_1$", *Immunol.,* 145:1687–1693, 1990.

Nagler–Anderson et al., "Suppression of Type II Collagen–Induced Arthritis By Intragastric Administration of Soluble Type II Collagen", *Proc., Natl. Acad. Sci.* USA, 83:7443–7446, 1986.

Powell, Jr. et al., "Neonatal Tolerance Induction By Class II Alloantigens Activates IL–4–Secreting, Tolerogen–Responsive T Cells", *Immunol.,* 144:854–859, 1990.

Sette et al., "A Novel Approach To The Generation of High Affinity Class II–Binding Peptides", *Immunol.,* 145:1809–1813, 1990.

Snapper et al., "IFN–γ Stimlates IgG2a Secretion by Murine B Cells Stimulated With Bacterial Lipopolysaccharide", *Immunol.,* 140:2121–2127, 1988.

Stuart, "Nature and Specificity of the Immune Response to Collagen in Type II Collagen–induced Arthritis in Mice", *J. Clin. Invest.,* 69:673–683, 1982.

Sun et al., "Functional Heterogeneity Among CD4 Encephalitogenic T Cells In Recruitment of CD8 T Cells In Experimental Autoimmune Encephalomyelitis", *Immunol.,* 143:2867–2872, 1989.

Terato et al., "Collagen–Induced Arthritis In Mice", 162:637–646, 1985.

Turnkin et al., "Key Antigenic Determinants In Regulation of the Immune Response", *Proc. Natl. Acad. Sci.* USA, 74:3984–3987, 1977.

Watson, "Genetic Susceptibility to Murine Collagen II Autoimmune Arthritis", *J. Exp. Med.,* 162:1878–1891, 1985.

White et al., "Two Better Cell Lines for Making Hybridomas Expressing Specific T Cell Receptors", *Immunol.,* 143:1822–1825, 1989.

Wooley, "Type II Collagen–Induced Arthritis In Mice", *J. Exp. Med.,* 154:688–700. 1981.

* cited by examiner

SEQUENCE LISTING (1) GENERAL INFORMATION:

(iii) NUMBER OF SEQUENCES: 9

(2) INFORMATION FOR SEQ ID NO: 1:

(i) SEQUENCE CHARACTERISTICS:
      (A) LENGTH: 11 amino acids
      (B) TYPE: amino acid
      (C) STRANDEDNESS: unknown
      (D) TOPOLOGY: unknown (ii) MOLECULE TYPE: peptide (vii) IMMEDIATE SOURCE:
          (B) CLONE: CII 260-270 [S260, 261, 263]

(ix) FEATURE:
          (A) NAME/KEY: Modified-si te
          (B) LOCATION: 2
          (D) OTHER INFORMATION: = "Xaa = 4-hydroxyproline"

(xi) SEQUENCE DESCRIPTION: SEQ ID NO: 1:

Ala Xaa Gly Asn Lys Gly Glu Gln Gly Pro L ys
1               5                   10

(2) INFORMATION FOR SEQ ID NO: 2:

(i) SEQUENCE CHARACTERISTICS:
          (A) LENGTH: 26 amino acids
          (B) TYPE: amino acid
          (C) STRANDEDNESS: unknown
          (D) TOPOLOGY: unknown (ii) MOLECULE TYPE: peptide (vii) IMMEDIATE SOURCE:
          (B) CLONE: CII 245-270 [260,261,263]

(ix) FEATURE:
          (A) NAME/KEY: Modified-si te
          (B) LOCATION: 17
          (D) OTHER INFORMATION: = "Xaa = 4-hydroxyproline"

(xi) SEQUENCE DESCRIPTION: SEQ ID NO: 2:

Pro Thr Gly Pro Leu Gly Pro Lys Gly Gln T hr Gly Glx Leu Gly Ala
1               5                   10                  15
Xaa Gly Asn Lys Gly Glx Gln Gly Pro Lys
            20                  25

(2) INFORMATION FOR SEQ ID NO: 3:

(i) SEQUENCE CHARACTERISTICS:
          (A) LENGTH: 26 amino acids
          (B) TYPE: amino acid
          (C) STRANDEDNESS: unknown
          (D) TOPOLOGY: unknown (ii) MOLECULE TYPE: peptide (vii) IMMEDIATE SOURCE:
          (B) CLONE: CII 245-270

(xi) SEQUENCE DESCRIPTION: SEQ ID NO: 3:

Pro Thr Gly Pro Leu Gly Pro Lys Gly Gln T hr Gly Glx Leu Gly Ile
1               5                   10                  15
Ala Gly Phe Lys Gly Glx Gln Gly Pro Lys
            20                  25

(2) INFORMATION FOR SEQ ID NO: 4:

(i) SEQUENCE CHARACTERISTICS:
          (A) LENGTH: 6 amino acids
          (B) TYPE: amino acid
          (C) STRANDEDNESS: unknown
          (D) TOPOLOGY: unknown (ii) MOLECULE TYPE: peptide (vii) IMMEDIATE SOURCE:
          (B) CLONE: CII 260-265 [S260, 261, 263]

```
    (ix) FEATURE:
         (A) NAME/KEY: Modified-site
         (B) LOCATION: 2
         (D) OTHER INFORMATION: = "Xaa = 4-hydroxyproline"

(xi) SEQUENCE DESCRIPTION: SEQ ID NO: 4:

Ala Xaa Gly Asn Lys Gly
1               5

(2) INFORMATION FOR SEQ ID NO: 5:

(i) SEQUENCE CHARACTERISTICS:
         (A) LENGTH: 26 amino acids
         (B) TYPE: amino acid
         (C) STRANDEDNESS: unknown
         (D) TOPOLOGY: unknown (ii) MOLECULE TYPE: peptide (vii) IMMEDIATE SOURCE:
         (B) CLONE: CII 245-270  [S248-249]

(ix) FEATURE:
         (A) NAME/KEY: Modified-site
         (B) LOCATION: 5
         (D) OTHER INFORMATION: = "Xaa= 4-hydroxyproline"

(xi) SEQUENCE DESCRIPTION: SEQ ID NO: 5:

Pro Thr Gly Ala Xaa Gly Pro Lys Gly Gln Thr Gly Glu Leu Gly Ile
1               5                  10                  15

Ala Gly Phe Lys Gly Glu Gln Gly Pro Lys
            20                  25

(2) INFORMATION FOR SEQ ID NO: 6:

(i) SEQUENCE CHARACTERISTICS:
         (A) LENGTH: 26 amino acids
         (B) TYPE: amino acid
         (C) STRANDEDNESS: unknown
         (D) TOPOLOGY: unknown (ii) MOLECULE TYPE: peptide (vii) IMMEDIATE SOURCE:
         (B) CLONE: CII 245-270  [s248, 251, 269]

(xi) SEQUENCE DESCRIPTION: SEQ ID NO: 6:

Pro Thr Gly Ala Leu Gly Ala Lys Gly Gln Thr Gly Glu Leu Gly Ile
1               5                  10                  15

Ala Gly Phe Lys Gly Glu Gln Gly Ala Lys
            20                  25

(2) INFORMATION FOR SEQ ID NO: 7:

(i) SEQUENCE CHARACTERISTICS:
         (A) LENGTH: 26 amino acids
         (B) TYPE: amino acid
         (C) STRANDEDNESS: unknown
         (D) TOPOLOGY: unknown (ii) MOLECULE TYPE: peptide (vii) IMMEDIATE SOURCE:
         (B) CLONE: CII 245-270  [S266, 267, 269]

(xi) SEQUENCE DESCRIPTION: SEQ ID NO: 7:

Pro Thr Gly Pro Leu Gly Pro Lys Gly Gln Thr Gly Glu Leu Gly Ile
1               5                  10                  15
```

```
Ala Gly Phe Lys Gly Asp Thr Gly Ala Lys
            20                  25
```

(2) INFORMATION FOR SEQ ID NO: 8:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: Type I 2 45-270

(ix) FEATURE:
        (A) NAME/KEY: Modified-si te
        (B) LOCATION: 5
        (D) OTHER INFORMATION: = "Xaa = 4-hydroxyproline"

(ix) FEATURE:
        (A) NAME/KEY: Modified-si te
        (B) LOCATION: 14
        (D) OTHER INFORMATION: = "Xaa = 4-hydroxyproline"

(ix) FEATURE:
        (A) NAME/KEY: Modified-si te
        (B) LOCATION: 17
        (D) OTHER INFORMATION: = "Xaa = 4-hydroxyproline"

(xi) SEQUENCE DESCRIPTION: SEQ ID NO: 8:

```
Pro Ser Gly Ala Xaa Gly Pro Lys Gly Asn S er Gly Glu Xaa Gly Ala
1               5                   10                  15

Xaa Gly Asn Lys Gly Asp Thr Gly Ala Lys
            20                  25
```

(2) INFORMATION FOR SEQ ID NO: 9:

(i) SEQUENCE CHARACTERISTICS:
        (A) LENGTH: 26 amino acids
        (B) TYPE: amino acid
        (C) STRANDEDNESS: unknown
        (D) TOPOLOGY: unknown (ii) MOLECULE TYPE: peptide (vii) IMMEDIATE SOURCE:
        (B) CLONE: CII 245-270  [s260, 261, 263]

(ix) FEATURE:
        (A) NAME/KEY: Modified-si te
        (B) LOCATION: 17
        (D) OTHER INFORMATION: = "Xaa = 4-hydroxyproline"

(xi) SEQUENCE DESCRIPTION: SEQ ID NO: 9:

```
Pro Thr Gly Pro Leu Gly Pro Lys Gly Gln T hr Gly Glx Leu Gly Ala
1               5                   10                  15

Xaa Gly Asn Lys Gly Glx Gln Gly Pro Lys
            20                  25
```

SYNTHETIC PEPTIDE FOR TREATMENT OF AUTOIMMUNE ARTHRITIS

This is a continuation of application Ser. No. 08/025,570, filed on Mar. 3, 1993 now abandoned.

FIELD OF THE INVENTION

The present invention provides peptides for suppressing autoimmune arthritis that do not provoke a material immunogenic response from T cells.

BACKGROUND OF THE INVENTION

Autoimmune arthritis afflicts a large number of people and takes many forms including, rheumatoid arthritis, juvenile arthritis, psoriatic arthritis, spondylo arthritis, relapsing polychondritis and other connective tissue diseases. These arthritic conditions occur in mammals when T cells are activated by particular antigens or complexes containing antigens. When such activation occurs, proteolytic enzymes are produced which degrade tissues of the person or mammal afflicted by arthritis. The tissue targets of autoimmune arthritis are constituents of connective tissues in joints and tendons of mammals and ordinarily include type II collagen. Indeed autoimmune arthritis can be induced in mice, humans and other mammal by immunizing them with type collagen II derived from cartilage of the same or different mammals. See, Andriopoulos N A, Mestecky J. Miller E J, Bradley E L: Antibodies to native and denatured collagen in sera of patients with rheumatoid arthritis. Arth. Rheum. 19:613–617, 1976; Wooley P H, Luthra S. Singh S. Huse A, Stuart J M, David C S: Passive transfer of arthritis in mice by human anti-type II collagen antibody. Mayo Clinic Proc. 59:737–743, 1984.

Autoimmune arthritis in mammals develops when T cells are activated by immunogenic complexes referred to as trimolecular complexes. These complexes are formed between antigenic peptides and major histocompatibility complex molecules (MHC). Buus, S., A. Sette, and H. M. Grey, (1987) "The interaction between protein-derived immunogenic peptides and Ia". *Immuno. Rev.* 98:115. These complexes then are recognized by the T cell receptors of antigen-specific T cells to form the tri-molecular complexes which result in the activation and subsequent functioning of T cells and in the development of arthritis.

Native type II collagen (CII) can induce arthritis in susceptible individuals. Certain fragments of native CII also induce an immunogenic response. Some of those immunogenic fragments and some of their analogs may also suppress the disease. Frequently this suppression occurs because T cell tolerance is developed. That is, the T cells are disabled from responding to the antigen or trimolecular complex containing the antigen. This immunogenic response (T cell tolerance) limits the therapeutic potential for the native polypeptide fragments and many of their analogs because the body develops immunity to the fragment after its first use. Subsequent treatments with the native fragments of CII are therefore expected to be ineffective. It would therefore be desirable to develop peptides that suppress autoimmune arthritis without inducing a material immunogenic response or, more preferably, without inducing any immunogenic response at all.

Peptides have been identified which may be capable of inhibiting specific T cell responses by blocking formation of the trimolecular complex in some way rather than by disabling the T cells. Babbitt, B. P., G. Matsueda, E. Haber, E. R. Unanue, and P. M. Allen, 1986, Antigenic Competition at the Level of Peptide-Ia Binding. *Proc. Natl. Acad. Sci. USA* 83:4509; Adorini, L. and Z. A. Nagy, 1990, Peptide Competition for Antigen Presentation. *Immuno. Today.* 11:21. Peptides have been used to suppress or prevent murine experimental autoimmune encephalomyelitis (EAE). Wraith, D. C., D. E. Smilek, D. J. Mitchell, L. Steinman, and H. O. McDevitt, 1989, Antigen Recognition in Autoimmune Encephalomyelitis and the Potential for Peptide-Mediated Immunotherapy. *Cell* 59:247; Lamont, A. G., A. Sette, R. Fujinami, S. M. Colon, C. Miles, and H. M. Grey, 1990, Inhibition of Experimental Autoimmune Encephalomyelitis Induction in SJL/J Mice By Using a Peptide with High Affinity for I-As Molecules. *J. Immunol.* 145:1687; Salao. K., S. S. Zamvil, D. J. Mitchell, S. Hodgkinson, J. B. Rothbard, and L. Steinman, 1989, Prevention of Experimental Encephalomyelitis with Peptides that Block Interaction of T Cells with Major Histocompatibility Complex Protein. *Proc. Natl. Acad. Sci. USA.* 86:9470. Investigators, using the EAE animal model, have demonstrated inhibition of the induction of experimental encephalomyelitis with synthetic peptides. When mice bearing the H-2$^u$ haplotype were co-immunized with an analog peptide and an encephalogenic peptide (amino acid residues 1–9 of myelin basic protein), disease did not develop. An unrelated peptide, known to bind to I-A$^S$, was used to inhibit the development of encephalomyelitis by the EAE-inducing antigen. Lamont, A. G., A. Sette, R. Fujinami, S. M. Colon, C. Miles, and H. M. Grey, 1990, Inhibition of Experimental Autoimmune Encephalomyelitis Induction in SJL/J Mice by Using a Peptide with High Affinity for I-As molecules. *J. Immunol.* 145:1687. The ability of some peptides to "compete" for binding to class II MHC molecules in vitro has been demonstrated. Werdelin, O, 1982, Chemically Related Antigens Compete for Presentation by Accessory Cells to T Cells. *J. Immunol.* 129:1883; Rock, K. L. and B. Benacerraf, 1984, Selective Modification of a Private I-A Allostimulating Determinant(s) Upon Association of Antigen With An Antigen-Presenting Cell. *J. Exp. Med.* 159:1238; Babbitt, B. P., G. Matsueda, E. Haber, E. R. Unanue, and P. M. Allen, 1986, Antigenic Competition at the Level of Peptide-Ia Binding. *Proc. Natl. Acad. Sci. USA* 83:4509.

The goal of providing peptides that block formation of trimolecular complexes without inducing material antigenic responses, however, is not always obtainable nor is success in obtaining that goal easily predictable. The strategy of developing a synthetic analog peptide having such a combination of features is not known to be a consistently reliable technique for developing therapeutically useful peptides in all autoimmune diseases or for autoimmune arthritis specifically. Two parameters that affect the ability of synthetic peptides to compete for antigen presentation are: 1) the relative affinity of antigenic and competitor peptides for the MHC molecule, and 2) the avidity of T cells for the activating ligand. One can not be reasonably assured of being able to develop a peptide which will have the required affinity and avidity for MHC yet that does not illicit a material immunogenic response from T cells.

In addition, use of analog peptides may make autoimmune arthritis worse rather than suppressing it in some instances. This problem occurs primarily when the analog stimulates T cell immunity. The resulting tolerance can subsequently break down. The disease then worsens and administration of the analog can not suppress it. This problem is particularly a concern with analogs of CII because the native CII fragments are known to be quite immunogenic and their analogs tend to also have a high level of immunogenicity. This makes more difficult and unlikely the development of analog peptides that suppress autoimmune arthritis without prompting an undesirable immunogenic T cell response.

SUMMARY OF THE INVENTION

The present invention provides analog peptides of fragments of CII protein, which contain a T cell antigen, which analog peptides suppress autoimmune arthritis. The analogs disrupt formation of trimolecular complexes of autoimmune antigenic peptide, MHC and T-cell receptor but do not provoke a material immunogenic response.

The present invention includes analogues of CII 245–270 and, more specifically, analogs of CII 260–270 peptide and of CII 245–270 [s 260, 261, 2631] peptide.

Moreover, the present invention provides the following peptides
  Sequence ID No. 4
  Sequence ID No. 1
  Sequence ID No. 2

DETAILED DESCRIPTION OF THE INVENTION

Figure 1:
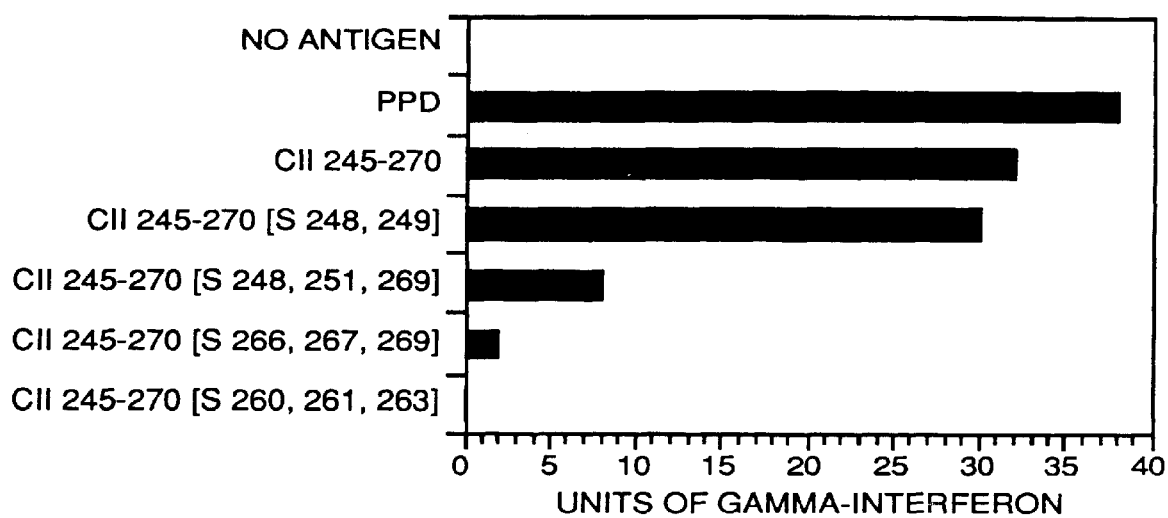
FIG. 1 shows the ability of various peptides to stimulate T cells. T cell stimulation is measured in units of γ-interferon production.

Applicants have now provided analog peptides to a fragment of type II collagen, (CII) that suppress autoimmune arthritis without inducing a material immunogenic response. The peptides appear to function as competitive inhibitors by binding to the I-A$^q$ molecule of MHC and in this way to interfere with or disrupt formation of the tri-molecular complex. The analogs of the present invention therefore suppress autoimmune arthritis by disrupting formation of trimolecular complexes. In addition to suppressing arthritis peptides of the present invention do not provoke a material immunogenic response. Peptides of the present invention are therefore useful therapeutic agents for suppressing autoimmune arthritis. They are expected to be useful in treatment of rheumatoid arthritis, juvenile arthritis, psoriatic arthritis, spondylo arthritis, relapsing polychondritis and other connective tissue diseases.

To develop and test the efficacy of synthetic peptides in suppression of autoimmune disease, native CII peptide, which is known to be immunogenic, was obtained. Fragments of the native peptide were then synthesized. Native CII was solubilized from the sterna of adult chickens by limited pepsin digestion. Stuart, J. M., M. A. Cremer, A. H. Kang, and A. S. Townes, 1979, Collagen-induced Arthritis in Rats: Evaluation of Early Immunologic Events, *Arthritis Rheum.* 22:1344. The disclosure of this article is incorporated by reference. Purified mαl(II) chains, obtained by thermally denaturing the CII, were subjected to non-enzymatic cleavage with cyanogen bromide and the resulting peptides isolated as described by Miller in Miller, E. J., 1971, Isolation and Characterization of the Cyanogen Bromide Peptides From the α1 (II) Chain of Chick Cartilage Collagen. *Biochemistry.* 10:3030. The disclosure of this article is incorporated herein by reference.

From the larger CII native peptide, a fragment identified as CII 245–270 has been identified as an important region of type II collagen (CII) in mice bearing the I-A$^q$ haplotype. The native amino acid sequence is:
  Sequence ID No. 3

This sequence is referred to herein as CII 245–270. This fragment is the same as to a comparable immunogenic fragment of human CII collagen with two exceptions. The comparable human sequence has alanine at position 245 and 4-hydroxyproline at position 258. There are no differences in the 260–270 region. Administration of CII 245–270 suppresses arthritis when used as a neonatal tolerogen. Myers, L. K., J. M. Stuart, J. M. Seyer, and A. H. Kang, (1989), "Identification of an Immunosuppressive Epitope of Type II Collagen that Confers Protection Against Collagen-Induced Arthritis" *J. Exp. Med.* 170:1999. The disclosure of that article is incorporated herein by reference. More recently, five residues, those numbered 260–265, have been identified which are important for T cell responses and tolerance. Myers, L. K., K. Terato, J. M. Seyer, J. M. Stuart, and A. H. Kang, 1992, "Characterization of a Tolerogenic T Cell Epitope of Type II Collagen and its Relevance to Collagen-induced Arthritis" *J. Immunol.* 149:1439. The disclosure of that article is incorporated herein by reference.

A number of analog peptides have been tested for their ability to competitively inhibit antigen presentation in vitro, and to prevent the development of collagen induced arthritis (CIA) in vivo. One preferred peptide competitively inhibits the T cell response to CII and significantly suppresses the development of arthritis when administered to DBA/I mice simultaneously with CII. The sequence of that preferred peptide, numbered to correspond to the native CII fragment disclosed above, is:
  Sequence ID No. 2

This peptide is referred to as CII 245–270 [s260, 261, 263]. (SEQ ID NO: 9) Smaller fragments of the foregoing peptide are expected to work in the same manner as long as a sufficient number of residues are present to inhibit formation of the trimolecular complex. In particular, the following peptides are expected to exhibit functional characteristics substantially identical to or very similar to the 26 residue analog disclosed above.
  Sequence ID No. 4
  Sequence ID No. 1

The shortest of the above sequences may also be referred to as CII 260–265 [s 260, 261, 263]. The larger of the two immediately proceeding sequences is also referred to as CII 260–270 [s 260, 261, 263].

In the development of the present invention, oligopeptides containing sequences corresponding to known sequences of α1(II)-CB11 were chemically synthesized by a solid-phase procedure described previously using an Applied Biosystem (model (430) peptide synthesizer. Seyer, J. M., K. A. Hasty, and A. H. Kang. (1989) "Covalent Structure of Collagen. Amino Acid Sequence of an Arthritogenic Cyanogen Bromide Peptide from Type II Collagen of Bovine Cartilage" *Eur. J. Biochem.* 181:151. Kanomi, H., J. M. Seyer, Y. Ninomiya, and B. R. Olsen. (1986) "Peptide-Specific Antibodies Identify the α2 Chain as the Proteoglycan Subunit of Type II Collagen" *J. Biol. Chem.* 261:6742. The sequence 1(II)-CBII is a large fragment of CII which includes the native fragment identified above as residues numbered CII 245–270, The disclosures of these two articles are incorporated by reference. The sequence of the chick CII gene was obtained and was used to deduce the entire CII protein sequence.

For peptide synthesis, protected tBoc amino acids were purchased from Applied Biosystems, Inc. (Foster City, Calif.) and coupled sequentially to a benzhydrylamine resin with a PAM linker. Deprotection was achieved with trifluoroacetic acid (25% in dichloromethane) and coupling was obtained in the presence of dicyclohexyl-carbodiimide. The completed synthetic peptide was cleaved from the resin and the side-chain protecting groups removed by treatment with liquid HF at 0° C. The desired peptide was initially purified by filtration through a SEPHADEX™ (cross-linked polysaccharide) G-25 column (4.0×60 cm) previously equilibrated with 0.1 M acetic acid. The effluent was collected in fractions of 10 ml. and aliquots taken from fluorescamine analysis. Fractions containing peptides were pooled, lyophilized, and further purified by reverse phase high pressure liquid chromatography on a Whatman ODS-3 (1 cm×25 cm) semipreparative column. Peptides were applied to the column in 0.05% trifluoroacetic acid and eluted over 30 min. with a gradient of 20–30% acetonitrile containing 0.05% trifluoroacetic acid at a flow rate of 2.0 ml/min. The effluent was monitored at 230 nm and the presence of peptides in relevant fractions confirmed by reaction with fluorescamine. The amino acid composition of the final peptide was determined using an automatic amino acid analyzer (Applied Biosystems, model 420A), and amino acid sequences were confirmed by automatic Edman degradation (Applied Biosystems, model 477). The amino acid composition found was ±5% theoretical, and the amino acid sequence analysis confirmed the peptide structure.

EXAMPLE I

Five specific residues of CII 245–270 have been identified as being particularly important for the stimulation of I-A$^q$-restricted T cells and the induction of tolerance. These are the residues numbered 260–270 above. Myers, L. K., K. Terato, J. M. Seyer, J. M. Stuart, and A. H. Kang, 1992, Characterization of a Tolerogenic T Cell Epitope of Type II Collagen and its Relevance to Collagen-Induced Arthritis. *J. Immunol.* 149:1439. To determine whether synthetic peptides containing amino acid substitutions at these positions might function as competitive inhibitors of antigen presentation to T cells, their ability to stimulate CII-primed T cells was examined. Four hexacosopeptides, analogs of CII 245–270, synthesized in the manner described above contained substitutions based on the type I collagen sequences or alanine substitutions for proline, as shown in Table I.

Table I. Amino Acid Sequence of Synthetic Peptides 245-270 [s266, 267, 269] is SEQ ID NO:7; Type I 245-270 is SEQ ID NO:8.

Type I collagen has a primary structure similar to CII, but immunization with type I collagen does not elicit (CIA). Nowarck H., E. Hahn, R. Timple, 1976, "Requirements for T Cells in the Antibody Response of Mice to Calf Skin Collagen," *J. Immunol.* 30:29. Each peptide was cultured with pooled spleen and lymph node cells from CII-immunized mice, and culture supernatant fluids were tested for the presence of γ-interferon as an indicator of T cell stimulation. T cell hybridomas were established by polyethylene glycol-induced fusion of lymph node cells with the T cell receptor α$^-$/β$^-$thymoma line, BW5147. White, M., M. Blackman, J. Bill, J. Kappler, P. Marrack, D. P. Gold, and W. Born, 1989, Two Better Cell Lines for Making Hybridomas Expressing Specific T Cell Receptors. *J. Immunol.* 143:1822. Marrack, P., 1982, Production of Antigen-Specific H-2 Restricted T Cell Hybridomas In "Isolation, Characterization, and Utilization of T Lymphocyte Clones", C. G. Fathman, and F. Fitch, eds. Academic Press, New York, N.Y., p. 508. The disclosures of each of these articles are incorporated by reference.

Lymph node cells were obtained from DBA/1 mice immunized with α1(II)-CB11 emulsified with complete Freund's adjuvant and cultured in vitro with α1(II)-CB11 for five days, and in the presence of IL-2 for three days before fusion. Hybridoma cells reactive to CB11 [CII 245–270] and CII were cloned by limiting dilution to 0.3 cells/well. Antigen presentation experiments were performed in 96 well microliter plates in a total volume of 0.3 ml containing $4 \times 10^5$ syngenic spleen cells and $10^5$ T-hybridoma cells. For competitive inhibition assays, spleen cells were pulsed with various ratios of inhibitor to indicator peptide and washed several times prior to addition to the antigen presentation culture. Cell cultures were maintained at 37° C. in 5% humidified $CO_2$ for 20 to 24 hours, after which seven 80 μl two-fold serial dilutions were made for determination of IL-2 titers. Four thousand HT-2 cells were added to each supernatant dilution, and after 16 to 20 hours HT-2 cell viability was evaluated by visual inspection. IL-2 titers were determined by the reciprocal of the highest two-fold serial dilution maintaining 90% viability of the HT-2 cells. Results are presented as units of IL-2 per ml of undiluted supernatant as described by Kapper et al. Kappler, J., J. White, D. Wegman, E. Mustain, and P. Marrack, 1982, Antigen Pre-

TABLE I

| Peptide§ | Amino acid sequence of synthetic peptides | | | | | | | | | | | | | | | | | | | | | | | | | |
|---|---|---|---|---|---|---|---|---|---|---|---|---|---|---|---|---|---|---|---|---|---|---|---|---|---|---|
| | 246 | | | | 250 | | | | 254 | | | | 258 | | | | 262 | | | | 266 | | | | 270 | |
| CII 245–270 | P | T | G | P | L | G | P | K | G | Q | T | G | E | L | G | I | A | G | F | K | G | E | Q | G | P | K |
| CII 245–270 [s248, 249] | — | — | — | A | B | — | — | — | — | — | — | — | — | — | — | — | — | — | — | — | — | — | — | — | — | — |
| CII 245–270 [s248, 251, 269] | — | — | — | A | — | — | A | — | — | — | — | — | — | — | — | — | — | — | — | — | — | — | — | — | A | — |
| CII 245–270 [s260, 261, 263] | — | — | — | — | — | — | — | — | — | — | — | — | — | — | A | B | — | N | — | — | — | — | — | — | — | — |
| CII 245–270 [s266, 267, 269] | — | — | — | — | — | — | — | — | — | — | — | — | — | — | — | — | — | — | — | — | D | T | — | A | — | — |
| Type I 245–270 | — | S | — | A | B | — | — | — | — | N | S | — | — | B | — | A | B | — | N | — | — | D | T | — | A | — |

§A "—" indicates identity at that position with native type peptide CII 245–270. Amino acid residues are represented by the single letter code. The letter "A" denotes Alanine, "B" denotes hydroxyproline, "D" denotes aspartic acid, "N" denotes asparagine and "S" denotes serine. Amino acid numbering system is based on the sequence of native CII.

CII 245-270 is SEQ ID NO:3; CII 245-270 [s248, 249] is SEQ ID NO:5; CII 245-270 [s248, 251, 269] is SEQ ID NO:6; CII 245-270 [s260, 261, 263] is SEQ ID NO:2; CII sentation by Ia$^+$B Cell Hybridomas to H-2 Restricted T Cell Hybridomas. *Proc. Natl. Acad. Sci. USA* 79:3604. The disclosure of this article is incorporated by reference.

T cell stimulation assays were performed in 96 well plates and the degree of stimulation was quantitated by measurements of γ-IFN production. Myers, L. K., K. Terato, J. M. Seyer, J. M. Stuart, and A. H. Kang, 1992, Characterization of a Tolerogenic T Cell Epitope of Type II Collagen and its Relevance to Collagen-Induced Arthritis. *J. Immunol.* 149:1439. The disclosure of this article is incorporated by reference. Spleens and lymph nodes from mice immunized with CII 14 to 21 days prior were individually minced into single cell suspensions in Hank's Balanced Salt Solution (BSS) and washed 3 times. $5 \times 10^5$ cells were cultured with 100 μm of antigen (synthetic peptides, collagen, or PPD) in 0.3 ml of Dulbecco's Modified Eagle Medium (Gibco, Gand Island, N.Y.) supplemented with 5% fetal bovine serum (Hyclone Laboratories, Logan, Utah). Supernatants were collected from 72 to 120 hours later and either 8 analyzed for γ-IFN production immediately or stored at −70° C. prior to analysis. Quantitative measurement of murine gamma interferon was done using a solid-phase enzyme-linked immunosorbent assay (Amgen Biologicals, Thousand Oaks, Calif.). Supernatant samples and standards were incubated in microliter plates coated with a monoclonal antibody recognizing murine γ-interferon. Plates were washed and incubated with a pre-formed detector complex consisting of a biotinylated second monoclonal antibody to γ-interferon and an anti-biotin-alkaline phosphatase conjugate. The absorbance was measured at 405 nm with a spectrophotometer, and a standard curve was obtained by plotting the absorbance versus the corresponding concentration of the standards. Units of γ-interferon were calculated based on NIH standard number Gg02-901-533. Each sample was tested in duplicate wells.

TABLE A

A test for measuring the production of interferon following stimulation of T-cells

| Preparation Steps | Step I | Immunize mouse with Type II collagen |
|---|---|---|
| | Step II | 14 to 21 days after Step I, mince spleens and lymph nodes from the mouse into single cell suspensions in Hank's BSS and wash 3 times |
| | Step III | Culture $5 \times 10^5$ of the cells of Step II with 100 μm of test antigen or a standard in 0.3 ml of Dulbecco's Modified Eagle Medium supplemented with 5% fetal bovine serum |
| | Step IV | Collect supernatant 72 to 120 hours after Step III |
| Assay Steps | Step I | Incubate supernatant sample and standard in microliter plates coated with a monoclonal antibody recognizing murine γ-interferon |
| | Step II | Wash plates and incubate with a pre-formed detector complex consisting of a biotinylated second monoclonal antibody to γ-interferon and an anti-biotin-alkaline phosphatase conjugate. |
| | Step III | Measure absorbance at 405 nm with a spectrophotometer |
| | Step IV | Obtain a standard curve by plotting the absorbance versus the corresponding concentration of the standards |
| | Step V | Calculate units of γ-interferon based on NIH standard number Gg02-901-533 |

As shown in FIG. 1, substitution of alanine for proline at position 248, and hydroxyproline for leucine at position 249 had almost no effect on T cell stimulation compared to the response of T cells to the wild type peptide, CII 245–270. However, when the substitution at residue 248 was combined with an alanine for proline substitution at residues 251 and 269, the ability of the T cells to respond to this peptide was greatly reduced (25% of the wild type peptide response), yet still above background levels. The measure of a material immunogenic response may vary in particular circumstances or for particular individuals. Generally, however, to provoke a material immunogenic response if more than about 5 units of interferon are measured by the foregoing test. In contrast, the CII-primed T cells did not respond to the analog peptides containing substitutions at residues 260, 261 and 263, and residues 266, 267, and 269 (FIG. 1).

All of these substitutions are based on type I collagen sequences, and are non-conservative substitutions, with the exception of the conservative substitution of aspartic acid for the glutamic acid at residue 266. These data indicated, among other things, that the amino acid(s) at positions 260–270 are important for I-$A^q$-restricted presentation of the CII 245–270 peptide to T cells.

EXAMPLE II

The inability of some analog peptides to stimulate T cells likely occurs either because of disruption of peptide binding to the I-$A^q$ molecule or the inability of the T cell receptor to recognize the peptide. In order to determine whether the analog peptides could bind to the class II molecule, competitive antigen presentation assays were performed. Antigen presenting cells (APC) were pulsed with various molar ratios of CII 245–270 and an analog peptide, and tested for their ability to stimulate CII 245–270 specific T cell hybridomas. When APC were competitively pulsed with the CII 245–270[s260, 261, 263] and CII 245–270 at molar ratios of 6:1 or greater, respectively, their ability to stimulate the T-cell hybridomas was greatly reduced (Table II).

TABLE II

| | | Competitive inhibition of antigen binding to I-$A^q$ on the surface on antigen presenting cells. | | | | |
|---|---|---|---|---|---|---|
| | | IL-2 U/ml Molar Ratio (Competitor: CII 245-270)§ | | | | |
| T-cell Hybrid | Competitor Peptide | 13:1 | 6.5:1 | 3.2:1 | 1.6:1 | 0:1 |
| qCII85.33 | CII 245-270 [s260, 261, 263] | —* | 40 | 320 | 640 | 640 |
| | CII 245-270 [s266, 267, 269] | 640 | 640 | 640 | 640 | 640 |
| 2qCII92.33 | CII 245-270 [s260, 261, 263] | — | 20 | 80 | 160 | 160 |
| | CII 245-270 [s266, 267, 269] | 160 | 160 | 160 | 160 | 160 |
| qCII98.10 | CII 245-270 [s260, 261, 263] | — | 40 | 80 | 160 | 160 |
| | CII 245-270 [s266, 267, 269] | 160 | 160 | 160 | 160 | 160 |

§DBA/1 spleen cells were pulsed with various molar ratios of analog peptide and CII 245-270, washed, and tested for their ability to present antigen to a set of CII 245-270 specific T-cell hybridomas. Production of IL-2 by the T-cell hybridomas was determined by the ability of culture supernatants to support the growth of IL-2 dependent cell line, HT-2.
*A "—" indicates less than 20 U/ml of IL-2 detected.

These data indicate that the analog peptide designated CII 245–270 [s260, 261, 263] is capable of binding to I-$A^q$. The amino acid substitutions in this peptide are believed to disrupt the ability of the T cell receptor to recognize the peptide. In contrast, the CII 245–270[s266, 267, 269] analog peptide did not compete for the presentation of the wild type peptide to the T-cell hybridomas.

EXAMPLE III

Figure 2A:
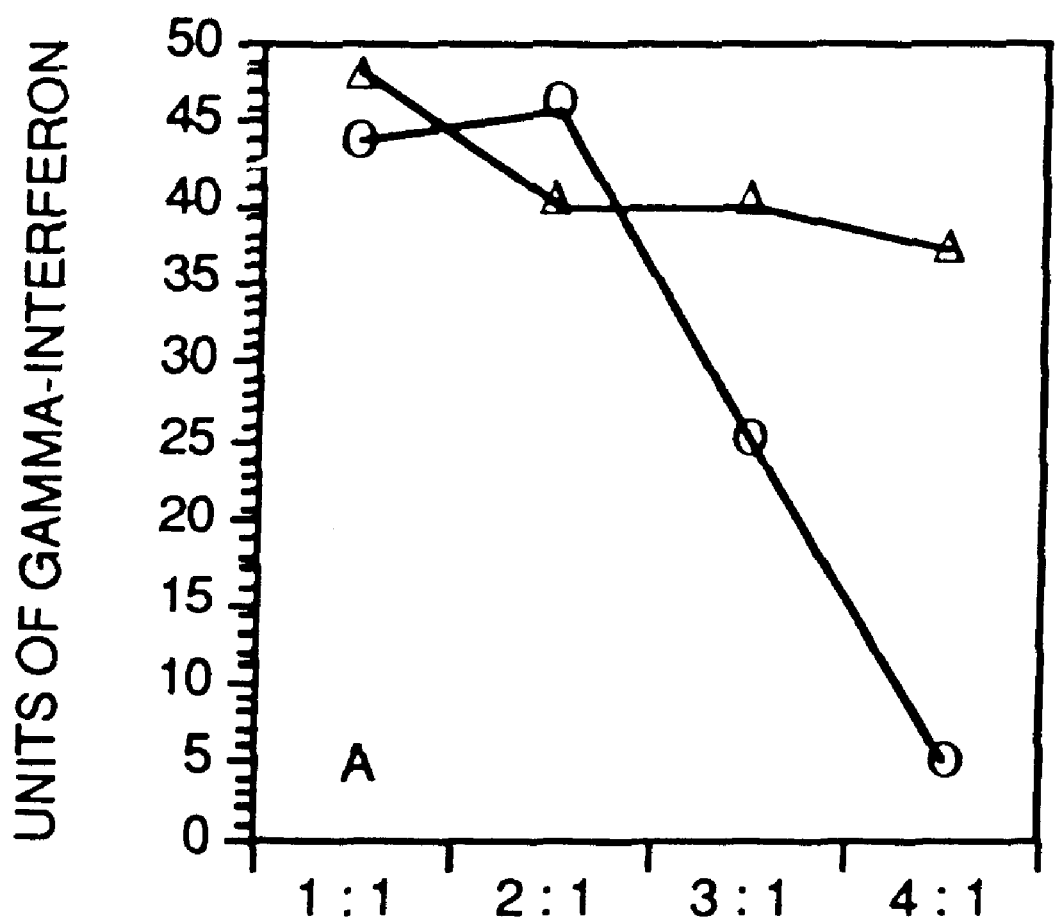
FIGS. 2A and 2B compare the ability of CII 245-270 [s260, 261, 263] (○) and CII 245-270 [s266, 267, 269] (▲) to stimulate T cells provided at various ratios: 1:1 to 4:1 (FIG. 2A); 40:1 to 320:1 (FIG. 2B).
Figure 2B:
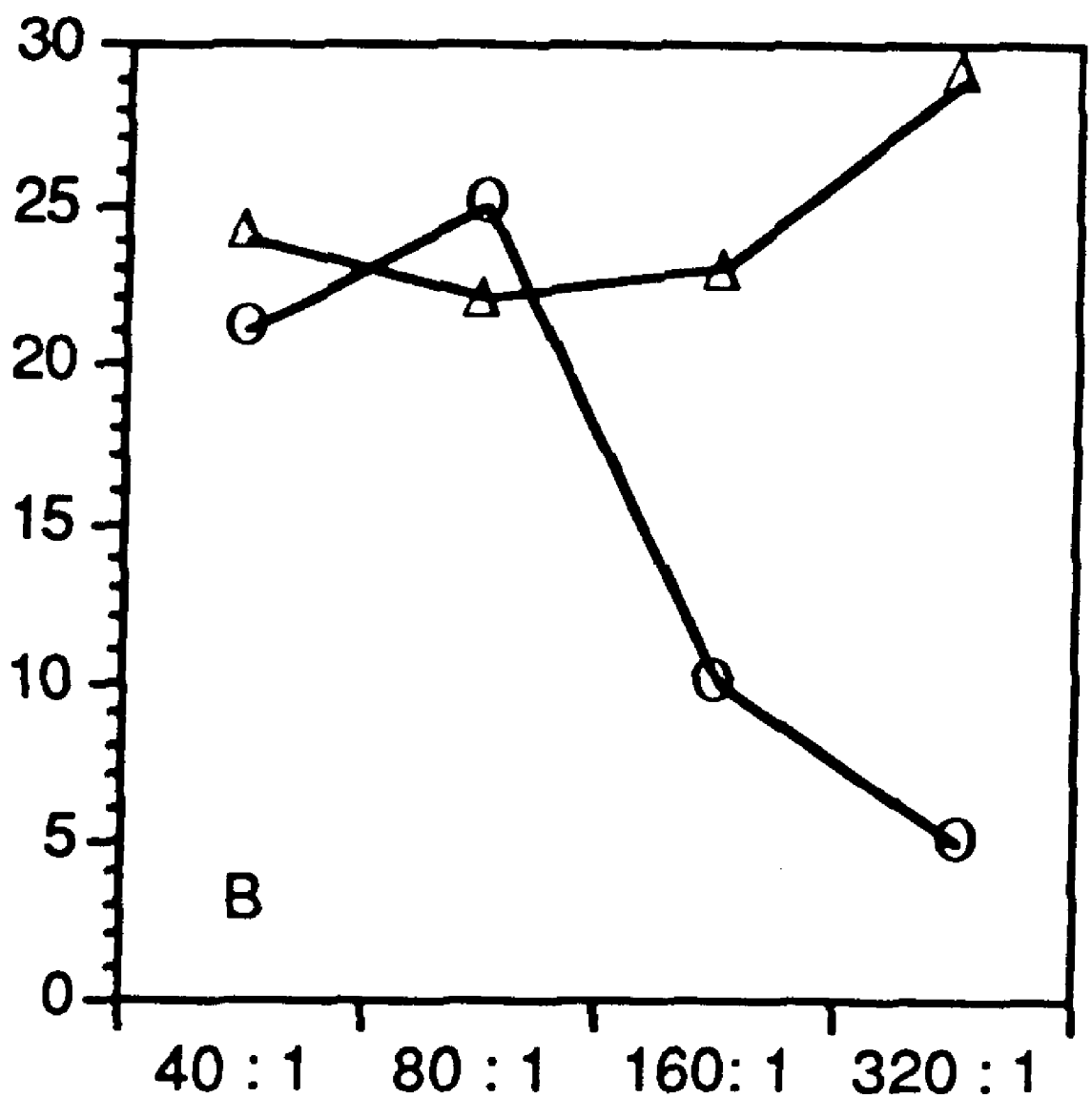

The same two analog peptides used in Example II were tested for their ability to inhibit the presentation of antigen to CII-primed, bulk T cells. Similar results were observed to those noted in Example II. In these experiments analog peptides were co-cultured with either CII 245–270 or native CII at various ratios with primed T cells from CII-immunized DBA/1 mice. As was observed with the T-cell hybridomas, the addition of peptide CII 245–270[s260, 261, 263] to the T cell cultures significantly decreased responses to both CII 245–270 and CII in a dose dependent manner while CII 245–270[s266, 267, 269] had no significant effect (FIG. 2).

The molar ratios required for inhibition were similar for the competitive presentation of the wild type peptide, and significantly higher molar ratios were required for the inhibition of the presentation of CII. This may reflect variation in the antigen processing required, or the differing numbers of class II binding determinants within the CII molecule and CII 245–270.

EXAMPLE IV

Since the analog peptide CII 245–270[260, 261, 263] inhibited the presentation of antigen in vitro, it was tested for its ability to inhibit the induction of experimental arthritis in vivo with DBA/1 mice. Arthritis induced in mice is considered a model for human rheumatoid arthritis. Anderson, Banerjee, Luthra and David, 1991, Role of Mls-1 Locus and Cloned Deletion of T Cells in Susceptibility to Collagen-Induced Arthritis in Mice, J. Imm. Vol. 147, 1189–1193.

DBA/1 mice, obtained from Jackson Laboratories (Bar Harbor, Me.), were maintained in groups of six in polycarbonate cages and fed standard rodent chow (Ralston Purina Co, St. Louis, Mo.) and water ad libitum. The environment was specific pathogen-free and sentinel mice were tested routinely for mouse hepatitis and Sendai viruses. Neonatal mice were obtained by breeding mice from Jackson Laboratories in our facility. Mice were immunized at 8–12 weeks of age. Stuart, J. M., A. S. Townes, and A. H. Kang, 1982. DBA/1 mice were immunized with either CII, CII plus CII 245–270, or CII plus CII 245–270[s260, 261, 263] at various molar ratios and were observed for the development of arthritis.

Mice were bled at four weeks after immunization and the serum was tested for antibodies reactive with type II collagen by enzyme-linked immunoassay (ELISA) described in Stuart, J. M., A. S. Townes, and A. H. Kang. 1982. Nature and Specificity of the Immune Response to Collagen in Type II Collagen-Induced Arthritis in Mice, *J. Clin. Invest.* 69:673. The disclosure of this article is incorporated by reference An anti-CII serum standard was used in each assay. A standard curve was derived by computer analysis using a 4 parameter logistic curve. Results are reported as units of activity, derived by comparison of test sera with the curve derived from the anti-CII standard which was arbitrarily defined as having 50 units of activity. Sera from mice were tested individually, and means were calculated for each experimental group.

Chick CH II obtained as described above, was dissolved in 0.01 N acetic acid and emulsified with an equal volume of complete Freund's adjuvant (CFA). In some experiments, a synthetic peptide was added to the emulsion in varying concentrations. That is, in coimmunization experiments synthetic peptide was added to the same emulsion as the native CII peptide. The resulting emulsion was injected intradermally into the base of the tail. Each mouse received a total volume of 0.005 ml containing 100 $\mu$g of MTb and 100$\mu$ of antigen.

To measure the incidence of arthritis in immunized mice, individuals examined and scored each of the forepaws and hind paws on a scale of 0–4 as described in Wooley, P. H., H. W. Luthra, J. M. Stuart and C. S. David. 1981. "Type 11 Collagen-induced Arthritis in Mice". I. Major Histocompatibility Complex (I region) Linkage and Antibody Correlates. *J. Exp. Med.* 154:688. This article is incorporated herein by reference. There were two separate examiners, one of whom was unaware of the identity of the treatment groups. Each mouse was scored three times a week beginning three weeks post immunization and continuing through 8 weeks post immunization. The incidence of arthritis (number of animals with one or more arthritic limbs) was reported at 6 weeks post immunization, the time point at which the control group reached its peak of disease. The incidence of arthritis in various groups of mice was compared using Fisher's Exact Test. Student's T test was used to compare means of antibody responses to CII.

DBA/1 mice co-immunized with CII 245–270[s260, 261, 263] demonstrated a dose-dependent decrease in the incidence of arthritis and number of arthritic limbs (Table III).

TABLE III

Suppression of Arthritis by Simultaneous Immunization with CII and an Analog Peptide

| Peptide§ | Molar Ratio (CII:Peptide) | Number of Arthritic Mice | Number of Arthritic Limbs |
| --- | --- | --- | --- |
| CII 245-270 | 110 | 10/12 (83%) | 24/48 (50%) |
| [s260-261, 263] | 1:160 | 4/6 (67%) | 10/24 (42%) |
|  | 1:320 | 6/12 (50%) | 11/48 (23%)** |
|  | 1:480 | 0/10 (0%)* | 0/40 (0%)** |
| CII 245-270 | 1:480 | 4/6 (67%) | 8/24 (33%) |

§DBA/1 mice were immunized intradermally with a single emulsion containing either CII 245-270[s260, 261, 263] and CII, or wild type CII 245-270 and CII in complete Freund's adjuvant.
*p ≦ .002 using Fisher's Exact Test.
**p ≦ .005 using Fisher's Exact Test When molar ratios of native CII to CII 245–270[s260, 261, 263] of 1:480, respectively, were co-injected, arthritis did not develop. Simultaneous immunization with CII plus CII 245–270 did not alter the incidence of disease.

In order to assess the effects of co-immunizing mice with both CII 245–270[s260, 261, 263] and CII, the mean antibody titers to native CII were measured for each immunization group in Table III, four weeks after immunization (Table IV).

TABLE IV

Measurement of anti-CII response in DBA/1 mice co-immunized with analog peptides and CII.

| Peptide | Molar Ratio (CII:peptide) | Antibodies to CII§ |
| --- | --- | --- |
| CII 245-270[s260, 261, 263] | (1:480) | 17 ± 3** |
| CII 245-270[s260, 261, 263] | (1:320) | 34 ± 22* |
| CII 245-270[s260, 261, 263] | (1:160) | 53 ± 25 |
| CII 245-270 | (1:480) | 54 ± 25 |
| None | (1:0) | 60 ± 20 |

§Serum was collected from mice co-immunized with the various peptides and CII, and antibody titers to type II collagen were tested using an ELISA.
*p ≦ .05 using Student's T test.
**p ≦ .005 using Student's T test.

Concordant with a decrease in the incidence and severity of arthritis, antibody production to native CII was also significantly decreased. These data indicate that peptide CII 245–270[s260, 261, 263] significantly down regulated the immune responses to CII in vivo as well as in vitro.

EXAMPLE V

The foregoing data support the hypothesis that analog peptide CII 245–270[s260, 261, 263] competes for binding to I-A$^q$. Further tests showed that the induction of T cell tolerance to CII 245–270 is not a likely explanation for the test results. Synthetic peptides were solubilized directly in phosphate buffered saline (PBS) at a concentration of 1 mg/ml. Neonatal mice were tolerized using a protocol described by Gammon et al.[21] in which antigen emulsified with incomplete Freund's adjuvant was injected intraperitoneally. Gammon, Dunn, Shastri, Oki, Wilbur, Sercarz, 1986, Neonatal T Cell Tolerance to Minimal Immunogenic Peptides is Caused by Clonal Inactivation, Nature (Lond) 319:413. The disclosure of this article is incorporated herein by reference. Each mouse received 100 μm of antigen in 0.1 ml of emulsion within 24 hours of birth. When they reached eight weeks of age, mice were immunized with CII and observed for arthritis as described above.

CII 245–270[s260, 261, 263] was administered to neonatal mice prior to immunization with CII, in order to induce tolerance and evaluate the effects on arthritis. While peptide CII 245–270 was an effective tolerogen, capable of inhibiting the subsequent induction of arthritis and also depressing the resulting mean antibody titers to CII, the analog was ineffective as a CII tolergen. It had no significant effect on either the development of arthritis or the development of antibodies to CII (Table V).

TABLE V

Inability of analog peptide to induce neonatal tolerance.

| Antigen§ | Number of Arthritic Mice | Antibodies to CII |
|---|---|---|
| No Antigen | 16/18 (89%) | 63.5 ± 25 |
| CII 245-270[s260, 261, 263] | 5/5 (100%) | 55.6 ± 19 |
| CII 245-270 | 6/20 (30%) | 18.5 ± 8* |

§Neonatal mice were injected intrapentoneally with 100 μg of antigen emulsified in incomplete Freund's adjuvant within 24 hours of birth. At eight weeks of age the mice were challenged with CII in CFA and observed for the development of arthritis. Serum was collected from the mice four weeks after immunization and mean antibody titers to CII were evaluated by an ELISA.

In vivo administration of a synthetic peptide, an analog of an antigenic determinant of type If collagen, successfully inhibited the development of collagen-induced arthritis. The simultaneous immunization of this analog peptide with CII not only reduced the incidence and severity of arthritis, but also significantly decreased the humoral immune response to collagen. In addition, the direct binding of the peptide to I-A$^q$ is currently believed to result in competitive inhibition of the T cell responses to CII. In this manner, peptides of applicants block formation of trimolecular complexes of autoimmune antigenic peptide, MHC and T cell receptors without provoking a material immunogenic response.

The data shown in Table II indicates that inhibition of CII 245–270-specific T cell responses occurs by competitive inhibition induced by direct binding of inhibitor to I-A$^q$. APC's prepulsed with competitor and antigen, then washed before culturing with antigen-specific T cell hybridomas, were ineffective at presentation of antigen. Since α1(II) is 40 times the size of CII 245–270 and likely contains a number of T cell antigenic sites, the greater molar ratio of the inhibitor peptide required to prevent T cell responses to α1(II) than to inhibit responses to CII 245–270 (FIG. 2B) indicates a mechanism in which the inhibitor binds to a site common to multiple antigenic peptides which are recognized by I-A$^q$-restricted T cells. Guery and coworkers, Guery, J. C., A. Sette, J. Leighton, A. Dragomir, and L. Adorini, 1992, Selective Immunosuppression by Administration of Major Histocompatibility Complex (MHC) class II-binding peptides. I. Evidence for In Vivo MCH Blockade Preventing T Cell Activation. J. Exp. Med. 175:1345, recently demonstrated that such a competition for class II binding may also occur in vivo. The disclosure of the foregoing article is incorporated herein by reference.

A toxic effect of the tested analog peptide is not likely, as T-cell hybrids specific for lysozyme in the context of 1-A$^k$, were not inhibited by CII 245–270[s260, 261, 263] when this peptide was added to cultures containing APC's and the HEL antigen. More specifically, the cells responded and were not killed. Data using peptide as neonatal tolerogens (Table V) also indicate that the analog peptide CII 245–270 [s260, 261, 263] is a very poor tolerogen. These data make the induction of antigen-specific tolerance unlikely, as a regulatory mechanism.

Administration of peptides of applicant's invention may occur through familiar techniques. In humans, the most likely routes are subcutaneous injection or oral administration. If subcutaneous injection is used, the peptide would be dissolved and injected with a pharmaceutically acceptable saline solution.

The foregoing disclosure illustrates currently preferred embodiments of applicants invention. It will be understood by those of ordinary skill in the art that modifications of the disclosed invention may be made without departing from the invention.

What is claimed is:

1. A method for supressing autoimmune arthritis comprising administering to a human patient an effective amount of a peptide comprising an amino acid sequence selected from the group consisting of Seq. ID No. 1 and Seq. ID No. 2.

2. The method of claim 1 wherein the peptide consists of an amino acid sequence selected from the group consisting of Seq. ID No. 1 and Seq. ID No. 2.

3. The method of claim 1 wherein the autoimmune arthritis is selected from the group consisting of rheumatoid arthritis, juvenile arthritis, psoriatic arthritis, spondyloarthritis, and relapsing polychondritis.

4. The method of claim 1 wherein the administration is by subcutaneous injection or oral administration.

5. The method of claim 1 wherein the peptide comprises the amino acid sequence of Seq. ID No. 2.

6. The method of claim 1 wherein the peptide comprises the amino acid sequence of Ser. ID No. 1.

7. The method for suppressing autoimmune arthritis comprising administering to a mammalian patient an effective amount of a peptide comprising an amino acid sequence selected from the group consisting of Seq. ID No. 1 and Seq. ID No. 2, wherein the autoimmune arthritis is selected from the group consisting of rheumatoid arthritis, juvenile arthritis, psoriatic arthritis, spondyloarthritis, and relapsing polychondritis.

8. The method of claim 7 wherein the peptide consists of an amino acid sequence selected from the group consisting of Seq. ID No. 1 and Seq. ID No. 2.

9. The method of claim 7 wherein the administration is by subcutaneous injection or oral administration.

10. The method of claim 7 wherein the peptide comprises the amino acid sequence of Seq. ID No. 2.

11. The method of claim 7 wherein the peptide comprises the amino acid sequence of Seq. ID No. 2.

* * * * *